United States Patent
Verbeek et al.

(10) Patent No.: US 6,592,571 B1
(45) Date of Patent: Jul. 15, 2003

(54) DRUG PUMP WITH SUTURE LOOPS FLUSH TO OUTER SURFACE

(75) Inventors: Maurice Theodore Yvonne Verbeek, Geleen (NL); Frans Philippens, Beek (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/578,138

(22) Filed: May 24, 2000

(51) Int. Cl.[7] ............................................. A61K 9/22
(52) U.S. Cl. ............................................. 604/890.1
(58) Field of Search .................... 604/890.1, 891.1, 604/892.1, 67; 424/422; 361/763; 128/260

(56) References Cited

U.S. PATENT DOCUMENTS

| | | | |
|---|---|---|---|
| 3,527,220 A | 9/1970 | Summers | 128/260 |
| 3,951,147 A | 4/1976 | Tucker et al. | 128/260 |
| 4,146,029 A | 3/1979 | Ellinwood, Jr. | 128/260 |
| 4,314,562 A | 2/1982 | Ware | 128/419 |
| 4,400,169 A * | 8/1983 | Stephen | 604/175 |
| 4,548,607 A | 10/1985 | Harris | 604/891 |
| 4,714,462 A | 12/1987 | DiDomenico | 604/67 |
| 4,718,893 A | 1/1988 | Dorman et al. | 604/67 |
| 4,772,263 A | 9/1988 | Dorman et al. | 604/132 |
| 4,778,452 A * | 10/1988 | Moden et al. | 604/175 |
| 4,781,695 A * | 11/1988 | Dalton | 604/175 |
| 4,838,887 A | 6/1989 | Idriss | 604/891.1 |
| 4,931,050 A | 6/1990 | Idriss | 604/891.1 |
| 4,978,338 A * | 12/1990 | Melsky et al. | 604/132 |
| 5,176,641 A | 1/1993 | Idriss | 604/133 |
| 5,207,666 A | 5/1993 | Idriss et al. | 604/891.1 |
| 5,395,324 A * | 3/1995 | Hinrichs et al. | 604/132 |
| 5,431,695 A * | 7/1995 | Wiklund et al. | 439/909 |
| 5,535,097 A | 7/1996 | Ruben et al. | 361/763 |
| 5,575,770 A * | 11/1996 | Melsky et al. | 604/131 |
| 5,632,729 A * | 5/1997 | Cai et al. | 604/175 |
| 5,647,855 A * | 7/1997 | Trooskin | 604/175 |
| 5,695,490 A * | 12/1997 | Flaherty et al. | 604/891.1 |
| 5,769,823 A | 6/1998 | Otto | 604/141 |
| 5,776,169 A | 7/1998 | Schroeppel | 607/36 |
| 5,792,104 A * | 8/1998 | Speckman et al. | 604/175 |
| 5,792,123 A | 8/1998 | Ensminger | 604/272 |
| 5,908,414 A | 6/1999 | Otto et al. | 604/891.1 |
| 6,213,973 B1 * | 4/2001 | Eliasen et al. | 604/175 |

* cited by examiner

Primary Examiner—Teresa Walberg
Assistant Examiner—Daniel Robinson
(74) Attorney, Agent, or Firm—Stephen W. Bauer; Curtis D. Kinghorn

(57) ABSTRACT

A pump for pumping drugs, medicaments or other liquids is disclosed in one embodiment having suture loops co-extensive with the outside surface of the pump. At least one depression is formed in the outside surface of the pump. A wire co-extensive with the outer dimensions of the pump passes over the depression forming a space between the wire and the outside surface of the pump in the depression. In this position, the wire forms a suture loop. The surgeon, when suturing the pump of the present invention in place within a pocket of tissue or other similar location, places a suture between the wire and the outside surface of the pump in the depression to secure the pump. In another embodiment, depressions are created in a pump and a soft material is placed in and attached to the depressions. A suture may then be placed through the material of the soft material and the tissue of the patient in a pocket in the tissue of the patient to affixed the pump in the pocket.

46 Claims, 11 Drawing Sheets

PRIOR ART

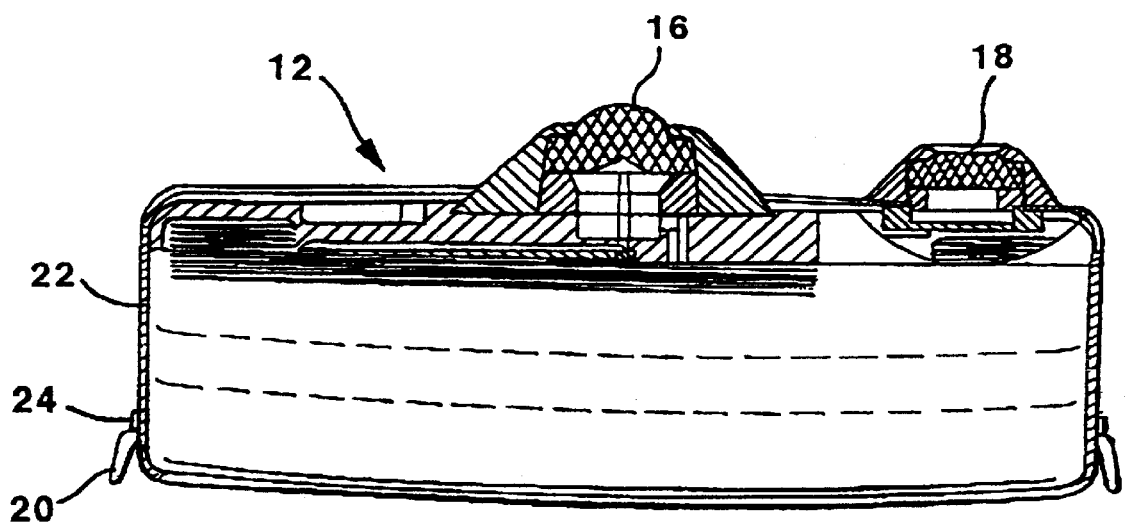
PRIOR ART  FIG. 3
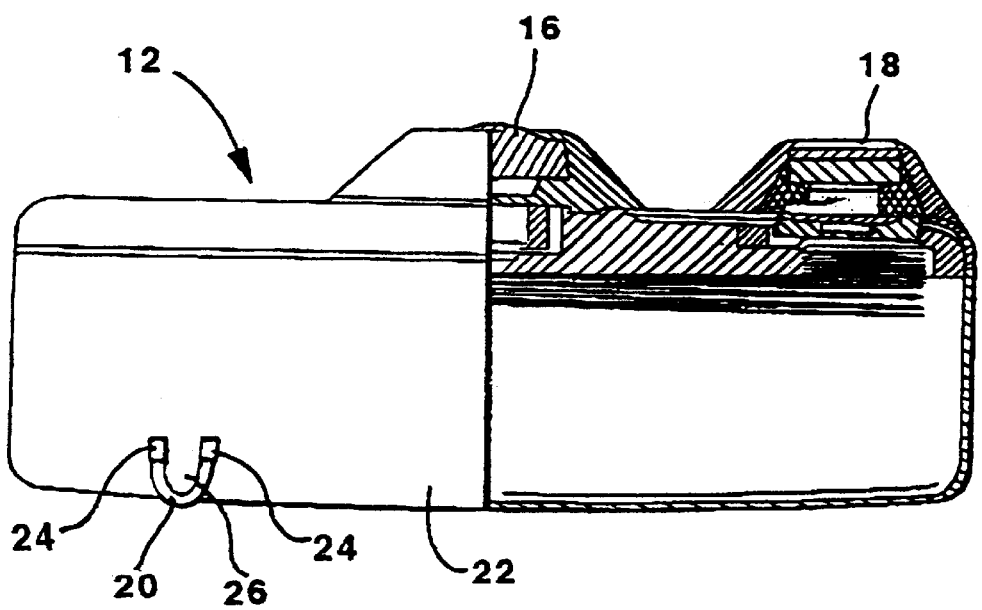
PRIOR ART  FIG. 4

DRUG PUMP WITH SUTURE LOOPS FLUSH TO OUTER SURFACE

BACKGROUND OF THE INVENTION

1. Field of the Invention

This invention relates to apparatus for delivering fluid drugs, medicaments or other medicinal liquids to a desired location within a human body and more particularly relates to means for securing such a device within a pocket of tissue of other similar location within a body.

2. Description of Related Art

A number of approaches have been followed in the prior art for the dispensing of medical substances in the body. One particularly effective method has been to implant a reservoir of fluid medical substances and a pump in a patient's body. The reservoir and pump are connected to a catheter that delivers the fluid medical substance to a desired location in the body.

A number of reservoirs, pumps and combinations of reservoirs and pumps have been developed. For example, U.S. Pat. No. 3,527,220 shows an implantable drug administrator that operates with a refillable bladder reservoir and a roller pump that is driven by a magnet located outside the body. U.S. Pat. No. 3,951,147 shows a reservoir formed from a bellows enclosed within a housing. The contents of the reservoir are pressurized by a fluorocarbon fluid located in the space between the housing and bellows. The unit continuously dispenses the liquid to the body site through a capillary tube.

U.S. Pat. No. 4,146,029 shows a dispenser that dispenses drugs in a predetermined manner which may be modified somewhat by means external to the body. A piston and bellows pumping device is used to dispense the drug.

Additional pumps and reservoirs are shown in U.S. Pat. No. 4,931,050, issued Jun. 5, 1990 to Samir F. Idriss entitled "Constant Pressure Variable Flow Pump"; U.S. Pat. No. 4,838,887, issued Jun. 13, 1989 to Samir F. Idriss entitled "Programmable Valve Pump"; U.S. Pat. No. 5,207,666, issued May 4, 1993 to Samir F. Idriss and Joshua Makower entitled "Passive Shuttle Metering Device For Implantable Drug Delivery System"; U.S. Pat. No. 4,714,462, issued Dec. 22, 1987 to Robert A. DiDomenico entitled "Positive Pressure Programmable Infusion Pump"; and U.S. Pat. No. 5,176,641 issued Jan. 5, 1993 to Samir F. Idriss entitled "Implantable Drug Infusion Reservoir Having Fluid Impelling Resilient Foam Member".

Further pumps and reservoirs are shown in U.S. Pat. No. 5,575,770 issued Nov. 19, 1996 to Gerald S. Melsky and Bradley J. Enegren entitled "Implantable Drug Infusion System With Safe Bolus Capability"; U.S. Pat. No. 4,978,338 issued Dec. 18, 1990 to Gerald S. Melsky and Frank R. Prosl entitled "Implantable Infusion Apparatus"; U.S. Pat. No. 5,908,414 issued Jun. 1, 1999 to Karl-Heinz Otto, Manfred Wieland, Hans Baumann and Jorg-Roger Peters entitled "Implantable Infusion Pump"; and U.S. Pat. No. 5,769,823 issued Jun. 23, 1998 to Karl-Heinz Otto entitled "Implantable Infusion Pump". The collective teachings of the patents listed above are incorporated herein in their entireties by reference.

A reservoir and pump system for storing and delivering fluid medicaments to a desired location in a body is shown schematically in FIG. 1 generally labeled 10. System 10 has a pump 12 that stores and dispenses fluid medicaments. A catheter 14 is connected to pump 12 and carries the fluid medicament from the pump 12 to a desired location in a body. The pump 12 and catheter 14 are implanted within the body.

Pump 12 typically has a primary septum 16 through which a drug, fluid or other medicament is placed in the pump 12. Pump 12 may also have a bolus septum 18 through which a bolus injection of drug, fluid or other medicament may be administered to the patient through the catheter 14.

Pump 12 is typically implanted in a body by creating a pocket in the tissue of the patient and placing the pump in the pocket. The pocket is often located under the skin in the abdomen below the rib cage. It is important that the pump 12 stay within the pocket so as not to migrate and maintain a desired orientation so as not to become separated from the catheter 14. To this end, the pump 12 is often sutured in the pocket to the surrounding tissue. In this way, the pump 12 cannot move within the pocket.

To facilitate the suturing, as shown in FIGS. 2–4, a series of suture loops 20 are placed on the outside of the pump 12. These suture loops 20 are typically made of wire that are fastened to the outside surface 22 of the pump 12 at each end 24 of each suture loop 20 by means such as welding. As a result, suture loops 20 are attached to the outside surface 22 of pump 12 at each end 24 of suture loop 20 and extend a small distance from the outside of pump 12 between the ends 24 of suture loop 20. As a result, a space 26 is formed between the outside surface 22 and the suture loops 20.

The surgeon, after placing pump 12 within the pocket "A" (FIG. 5), places a suture through the tissue and through the space 26 formed between the outside surface 22 and the suture loop 20 and ties a knot to secure the pump in a fixed position relative to the pocket. Because the suture is placed between the outside surface 22 and the suture loop 20, the suture is constrained to remain in the space 26. As a result, as the surgeon snugs up the suture and ties the knot, the suture is brought into taught engagement with the suture loop 20 whereby the pump is securely positioned.

One problem with this configuration is that suture loops 20 extend away from the outside surface 22 of pump 12. As a result, the ultimate dimensions of pump 12 with suture loops 20 are enlarged from the dimensions of the outside surface 22 of pump 12 itself. This then requires a slightly larger pocket to be created to hold the pump 12 with the suture loops 20 than would be necessary if pump 12 without the suture loops 20 were used. Further, the protruding suture loops 20 sometimes jab into and irritate the tissue of the pocket surrounding the suture loops 20. These are problems in want of a solution.

SUMMARY OF THE INVENTION

A pump for pumping drugs, medicaments or other liquids is disclosed in one embodiment having suture loops co-extensive with the outside surface of the pump. At least one depression is formed in the outside surface of the pump. A suture loop, preferably in the form of a wire, co-extensive with the outer dimensions of the pump passes over the depression forming a space between the wire and the outside surface of the pump in the depression. In this position, the wire forms a suture loop. The surgeon, when suturing the pump of the present invention in place within a pocket of tissue or other similar location, places a suture between the wire and the outside surface of the pump in the depression to secure the pump.

In an alternate embodiment, depressions are created in a pump and a soft material is placed in and attached to the depressions. A suture may then be placed through the material of the soft material and the tissue of the patient in a pocket in the tissue of the patient to affixed the pump in the pocket.

It is therefore an object of the present invention to provide a pump that may be sutured in a pocket of tissue of other similar location in a body where the pump does not have any substantial protrusions from its outside surface to facilitate the pump being sutured in the desired location.

It is another object of the invention to provide a system to facilitate suturing the pump in place in a desired location that is relatively easy to manufacture.

These and other objects of the invention will be clear from the description of the invention contained herein and more particularly from the description in conjunction with the drawings attached hereto. Throughout this description, wherever referred to, like elements are referred to by like reference numbers.

BRIEF DESCRIPTION OF THE DRAWINGS

The advantages of the present invention will become more apparent by referring to the following detailed description and accompanying drawings, in which:

FIG. 3 is a side cut-away of the drug pump and suture loops of FIG. 2.

FIG. 4 is a side partial cut-away view of the drug pump and suture loops of FIG. 2.

DESCRIPTION OF THE PREFERRED EMBODIMENT

Figure 1:
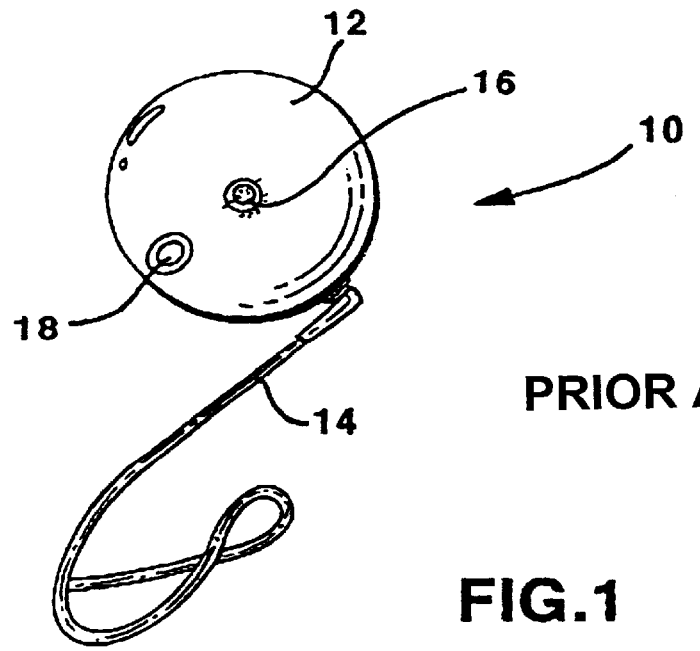
FIG. 1 is a schematic view of a typical pump and catheter.
Figure 2:
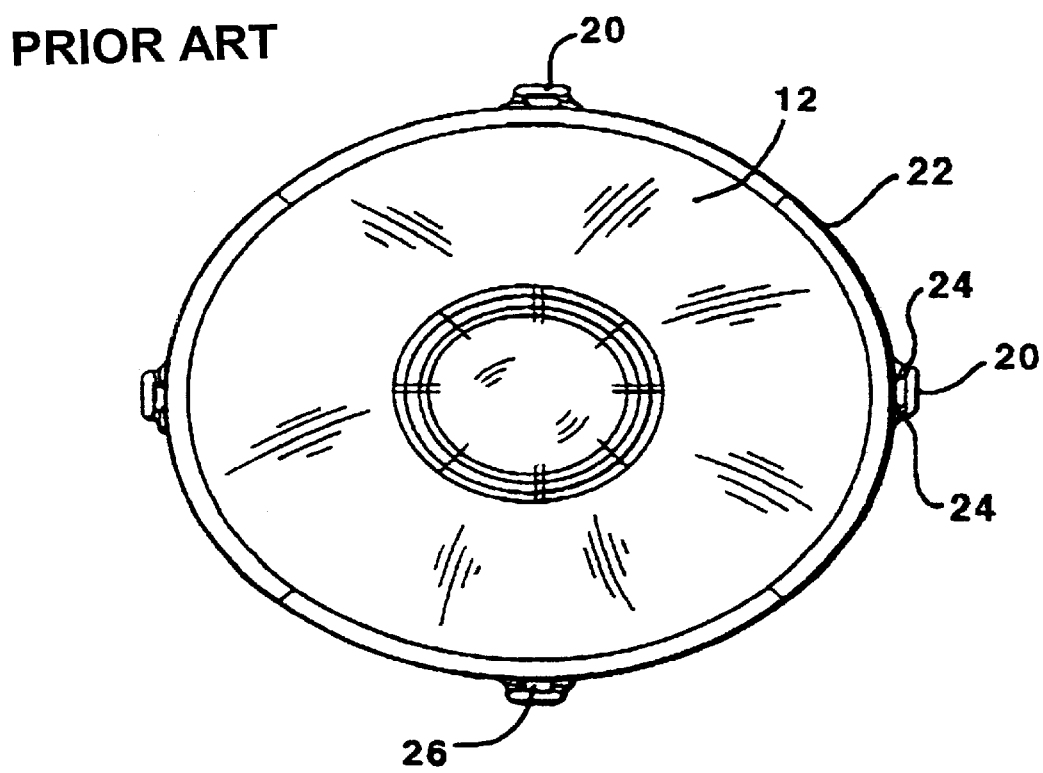
FIG. 2 is a top view of a drug pump with a series of prior art sutures loops.
Figure 5:
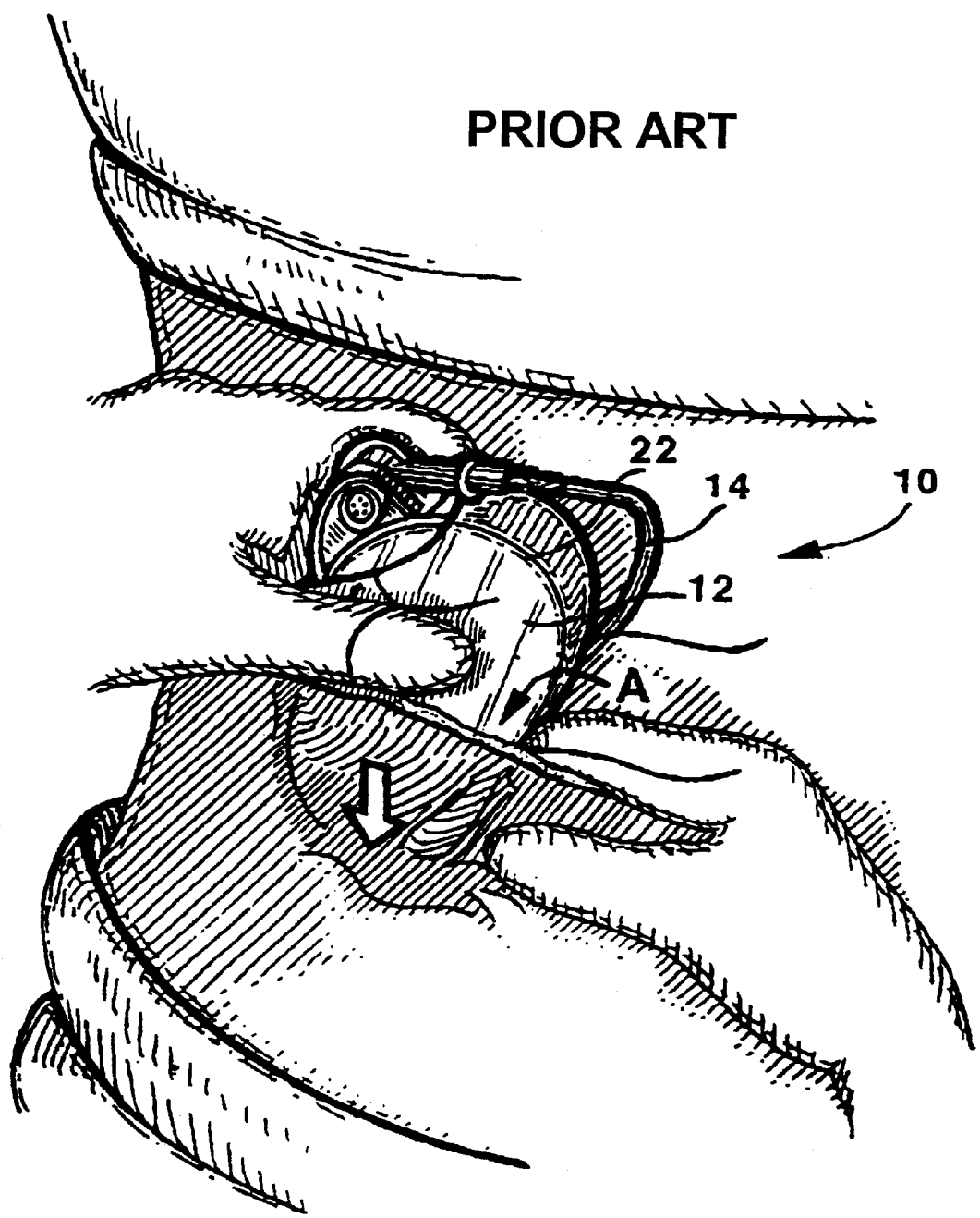
FIG. 5 is a perspective view of the drug pump of FIGS. 2–4 being placed in a pocket in tissue.

Referring now to FIGS. 6–11, a drug pump 12 incorporating the present invention is shown. As can be seen, pump 12 has an outside surface 22, an interior 28 and central axis 30. In the embodiment shown in FIGS. 6–11, pump 12 is substantially disk shaped. As such, outside surface 22 has a side wall 32 and a lower surface 34 connected to the side wall 32 by a lower edge 36 which transitions the side wall 32 to the lower surface 34. In this embodiment, outside surface 22 also has an upper surface 38 connected to side wall 32 by an upper edge 40 which transitions the side wall 32 to the upper surface 38. In this embodiment, side wall 32 is roughly equidistant from the central axis 30.

Although pump 12 is shown as being disk shaped to illustrate the present invention, this is not a requirement for the present invention. In fact, any shape for pump 12 may make use of the present invention so long as pump 12 has an outside surface 22. In pumps that are not disk shaped, central axis 30 merely indicates an approximate center of pump 12.

Figure 6:
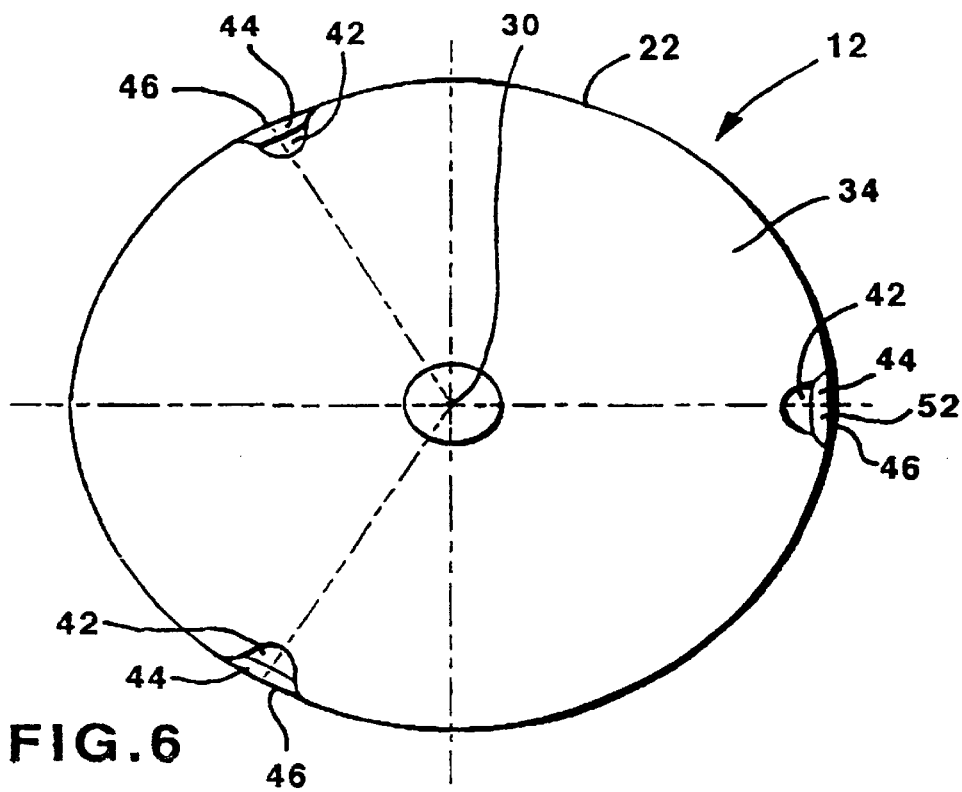
FIG. 6 is a bottom view of a drug pump with the suture loops of the present invention.
Figure 7:
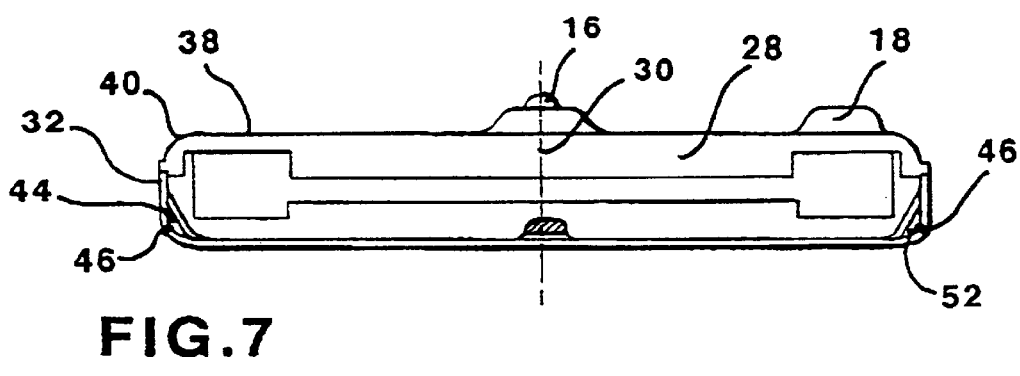
FIG. 7 is a side cross-sectional view of the drug pump and suture loops of FIG. 6.
Figure 8:
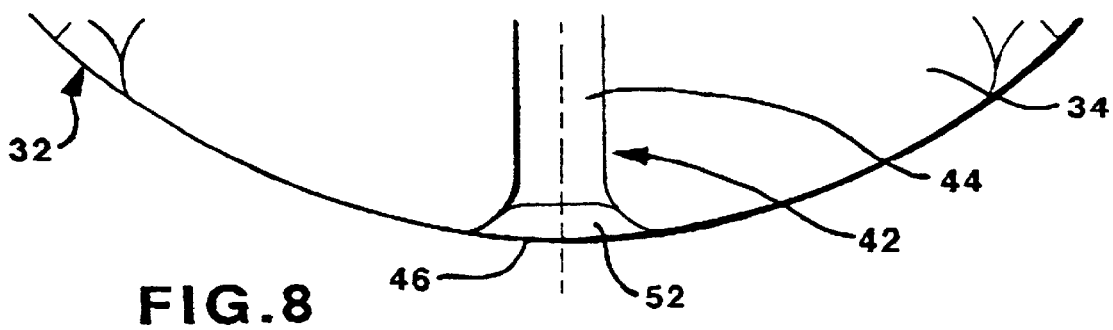
FIG. 8 is a close-up bottom view of the drug pump and suture loops of FIG. 6.
Figure 9:
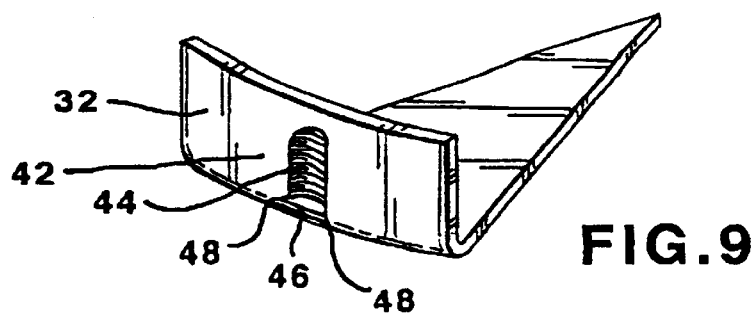
FIG. 9 is a cutaway perspective view of a portion of the drug pump and suture loops of FIG. 6 showing the suture loops.
Figure 10:
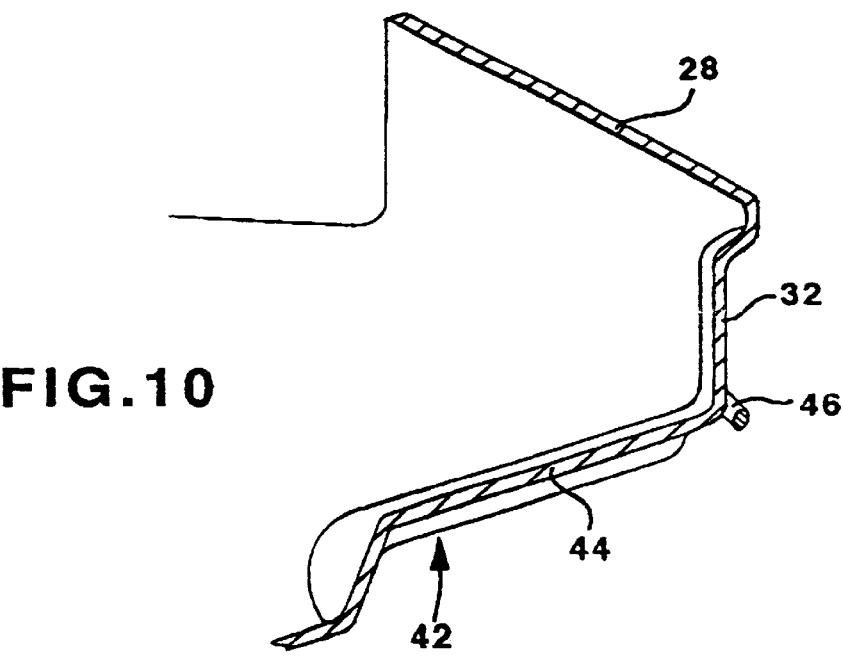
FIG. 10 is a cutaway perspective view of a cross-section of the drug pump and suture loops of FIG. 6.
Figure 11:
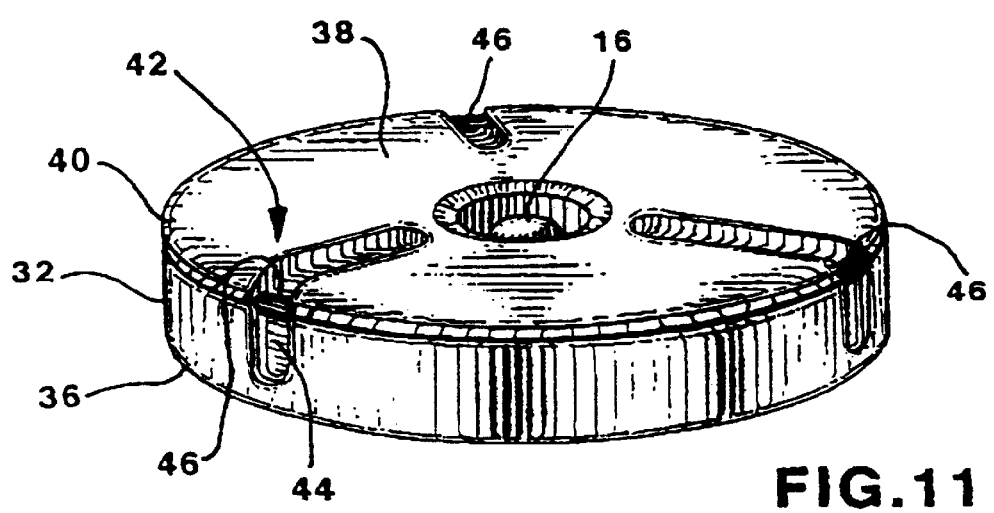
FIG. 11 is a perspective view of the drug pump and suture loops of FIG. 6.
Figure 13:
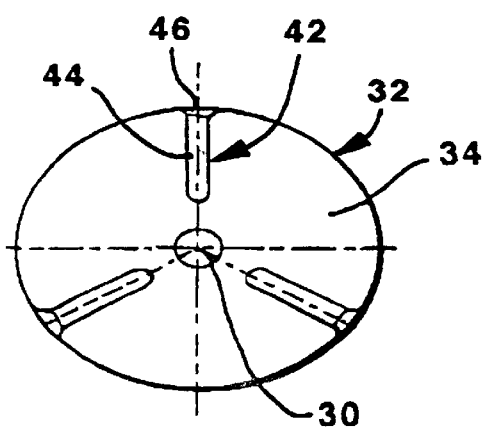
FIG. 13 is a bottom view of an alternate embodiment of the drug pump and suture loops of FIG. 6.
Figure 14:
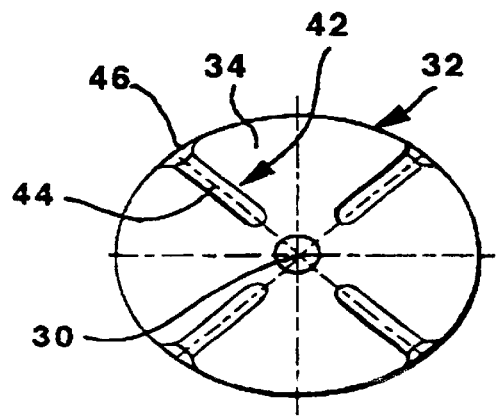
FIG. 14 is a bottom view of an alternate embodiment of the drug pump and suture loops of FIG. 6.
Figure 15:
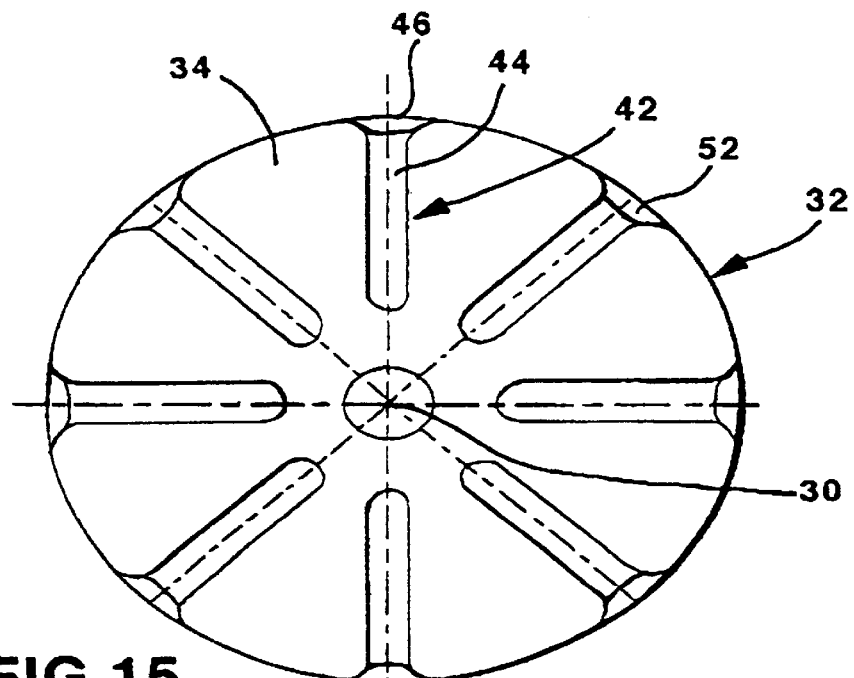
FIG. 15 is a bottom view of an alternate embodiment of the drug pump and suture loops of FIG. 6.

In the present invention, the outside surface 22 of pump 12 contains at least one depression 42 that extends inwardly from the outside surface 22 toward the interior 28. In the preferred embodiment, several depressions 42 are located at sites on the outside surface 22 desirable to form suture connections between the pump 12 and the tissue surrounding the pump 12 when the pump 12 is implanted. For example, FIG. 6 shows three depressions 42 equally spaced around the outside surface 22. More or fewer depressions 42 may be used as desired as shown in FIGS. 13–15, to show but a few variants, and the depressions 42 may also be non-equally spaced.

Figure 12:
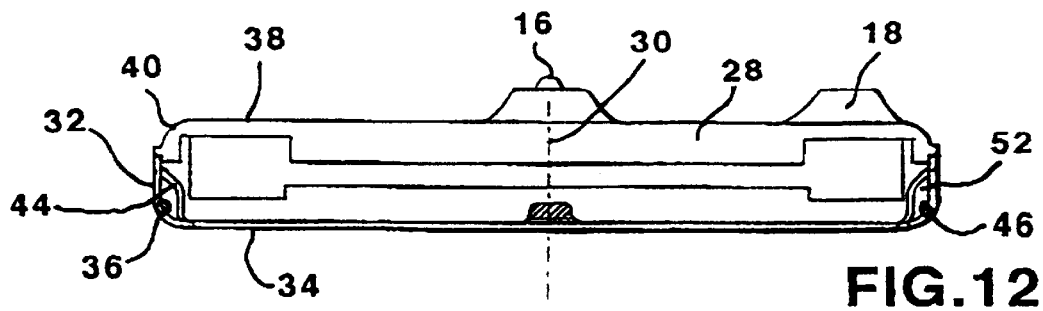
FIG. 12 is a cross-sectional side view of an alternate embodiment of the drug pump and suture loops of FIG. 6.

Depressions 42 are preferably shallow depressions in the outside surface 22 forming a depression surface 44. In the embodiment shown in FIGS. 6–11, depressions 42 are formed in the lower edge 36 where the side wall 32 of pump 12 transitions to the lower surface 34 of pump 12. In the embodiment shown in FIGS. 6–11, the depression surface 44 is convex with respect to the interior 28 of pump 12. Alternately, the depression surface 44 may be concave with respect to the interior 28 of pump 12 as shown in FIG. 12 or any other shape so long as a space exists between the depression surface 44 and the outside surface 22.

Figure 16:
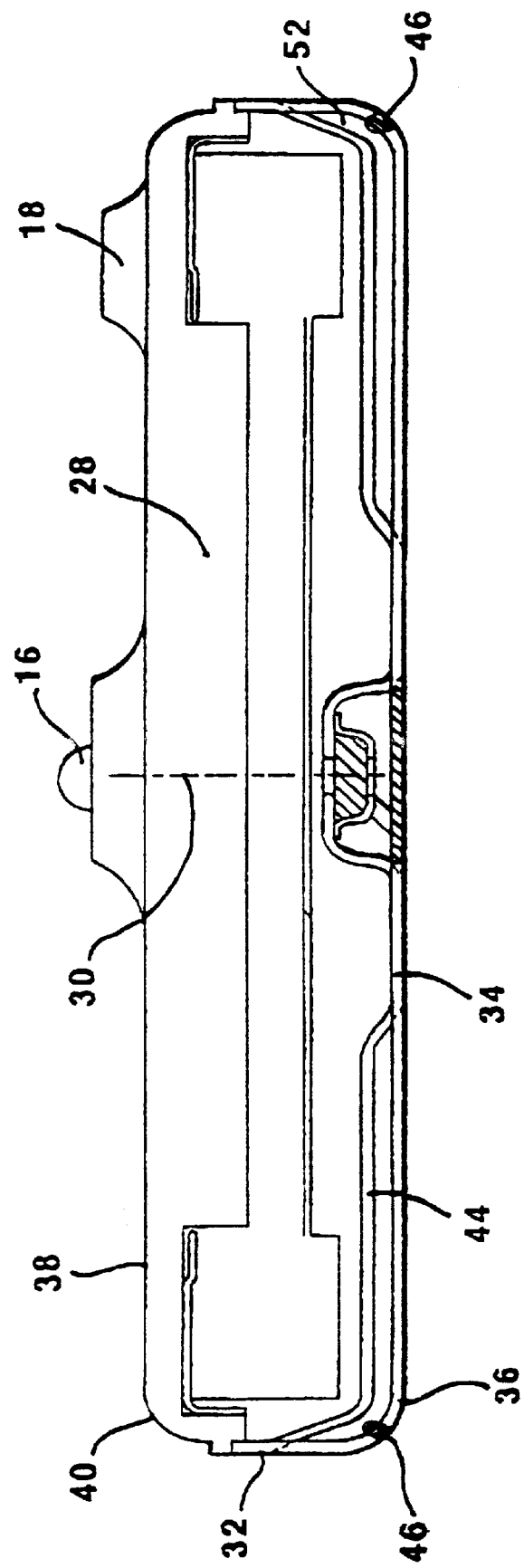
FIG. 16 is a cross-sectional side view of the alternate embodiments of the drug pump and suture loops of FIGS. 13–15.

Depressions 42 may also be formed in the upper edge 40 where the side wall 32 transitions to the upper surface 38 of pump 12. Alternately, depressions 42 may also be formed directly in the side wall 32, lower surface 34 or upper surface 38 of pump 12. Where depressions 42 are formed in the lower surface 34 or upper surface 38, depressions 42 may extend only a short distance toward the central axis 30 of the pump 12 as shown in FIGS. 6–11 or may extend a significant distance toward the central axis 30 of pump 12 as shown in FIG. 16.

As stated above, depressions 42 may take any form so long as the depression surface 44 is moved toward the interior 28 of pump 12 from the ordinary outside surface 22 of the pump 12. For example, depressions 42 make take the form of semi-spherical depressions or truncated discoid depressions to name but a possible few configurations in addition to the trough-like depressions 2 shown in FIGS. 6–11. Whatever the form of depressions 42, the primary function of depressions 42 is to form a shallow depression from the outside surface 22. In this way, the outside surface 22 is substantially unchanged in its grossest dimensions, having only a series of shallow depressions forming the depressions 42.

A suture loop 46 extends across the space in the outside surface 22 created by the depression. Suture loop 46 is co-extensive with the outside surface 22 surrounding the depression 42. "Co-extensive" means that suture loop 46 is located where the outside surface 22 would have been had the depressions 42 not been formed in the outside surface 22. In this way, suture loops 46 are substantially flush with the outside surface 22 and the dimensions of pump 12 are not significantly enlarged, if enlarged at all, by the addition of suture loops 46.

Suture loops 46 are preferably made of a metal wire. In one embodiment, suture loops 46 are placed individually across the depressions 42 by welding or otherwise attaching the ends 48 of a short piece of wire to the outside surface 22 across each depression 42. Suture loops 46 may also be made of plastic, composites or any other material capable of spanning the depressions 42 and capable of being attached to the outside surface 22 and being strong enough to allow a surgeon to suture around the suture loop 46 to secure the pump 12.

Figure 17:
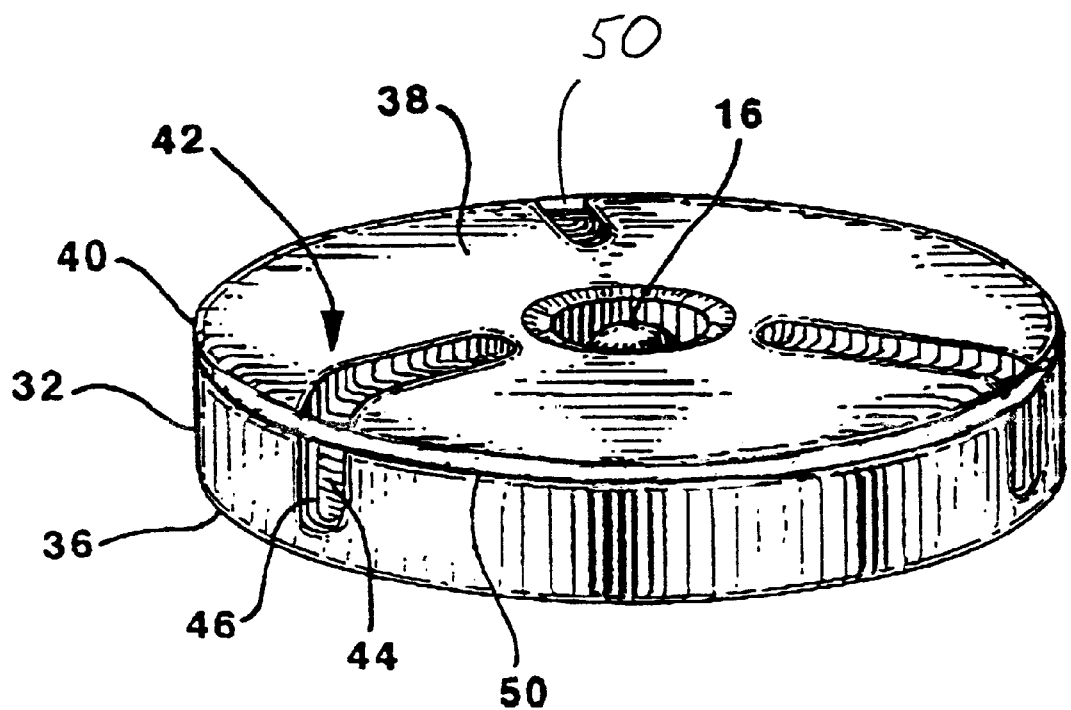
FIG. 17 is a perspective view of an alternate embodiment of the invention.

Alternately, as shown in FIG. 17, a single longer wire 50 can be laid over the outside surface 22 so that the wire 50 crosses the space created by each depression 42. This longer wire 50 is then welded or otherwise connected to the outside surface 22 to hold it in a fixed relation to the outside surface 22 and the depressions 42.

Regardless of the embodiment of suture loop 46 described herein according to the invention, a space 52 is created between the suture loop 46 and the depression surface 44 of depression 42. This allows the surgeon to place a suture between the suture loop 46 and the depression surface 44 to hold the pump 12 in place in a pocket in tissue.

Figure 18:
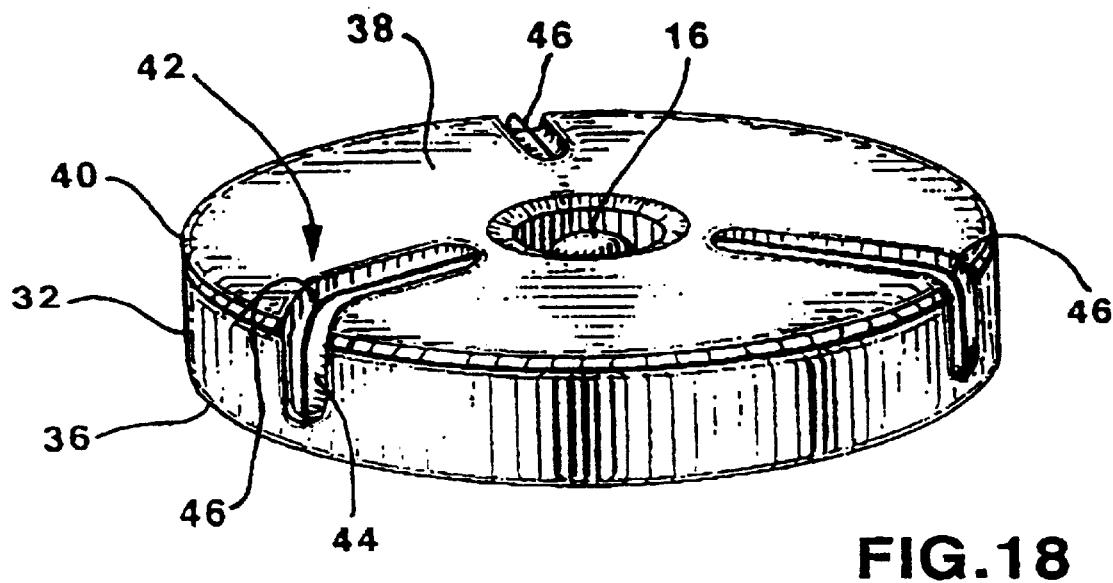
FIG. 18 is a perspective view of an alternate embodiment of the drug pump and suture loops of the invention.
Figure 19:
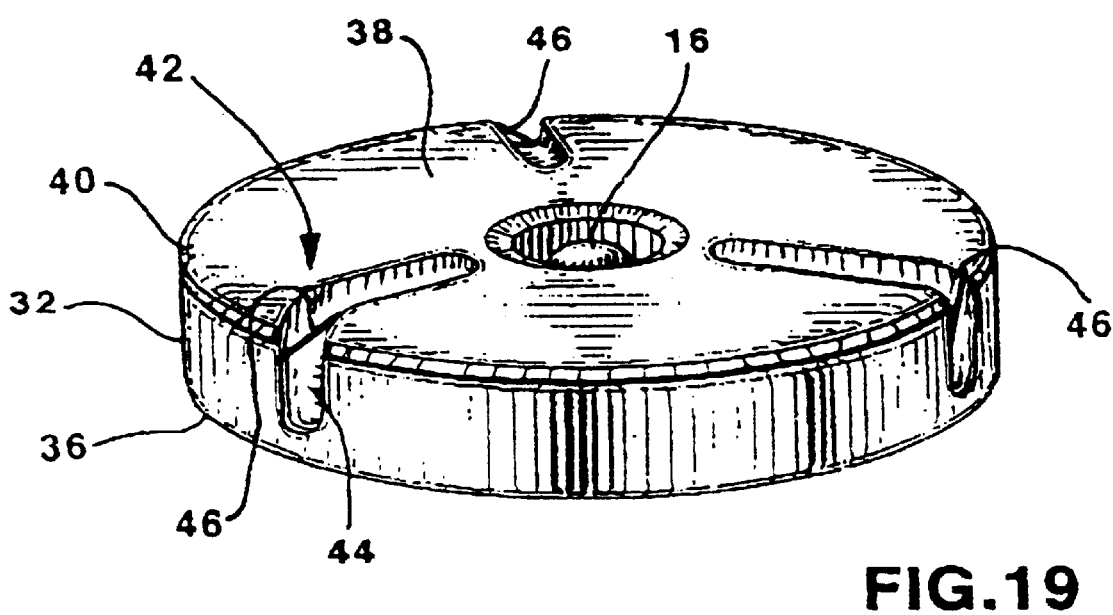
FIG. 19 is a perspective view of another alternate embodiment of the drug pump and suture loops of the invention.

Even though the suture loops 46 described above and shown in FIGS. 6–17 have been essentially horizontal, suture loops 46 need not be horizontal. For example, as shown in FIGS. 18 and 19, suture loops 46 may be vertical or diagonal, respectively. Further, individual suture loops 46 may be either horizontal, vertical or diagonal regardless of the configuration of the other suture loops 46 on the same pump 12. Whatever the configuration of suture loops 46, the key to suture loops 46 is that the suture loops 46 are substantially co-extensive with the outside surface 22 of the pump 12 and that a space 52 is created between the suture loop 46 and the depression surface 44 of the depression 42.

In the embodiments disclosed above having a suture loop 46, only a single suture loop 46 for each depression 42 has been disclosed. However, it is within the scope of the invention to have more than one suture loop 46 at a single depression 42 as desired.

Figure 20:
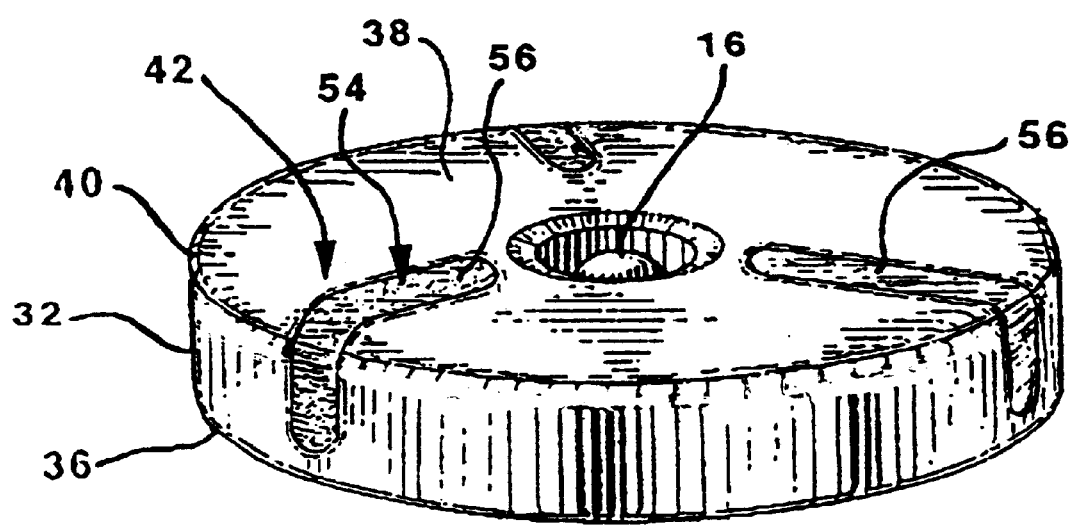
FIG. 20 is a perspective view of another alternate embodiment of the drug pump and suture securing system of the invention.

In a further alternate embodiment, as shown in FIG. 20, depressions 42 are created in pump 12 as described above. However, instead of a suture loop 46 as described above, a soft material 54 having an outer surface 56 is placed in and attached to depressions 42. A suture may then be placed through the material of soft material 54 and the tissue of the patient in the pocket A in the tissue of the patient to affixed the pump 12 in pocket A.

Soft material 54 may take the form of ETR silicone (Extra Tear Resistant), a polymer such as polyurethane, polytetrafluoroethylene, polyamide (Nylon) or a polyester such as Dacron or any other material capable of being bonded to or otherwise fixed in depressions 42 and capable of holding a suture therethrough without tearing. Soft material 54 is preferably affixed to depression surface 44 of depressions 42. This affixing is preferably done by adhesives although other means, as will be clear to those skilled in the art, may be used. Alternately, soft material 54 may be affixed directly to the outside surface 22 of pump 12 while residing in depressions 42.

Figure 21:
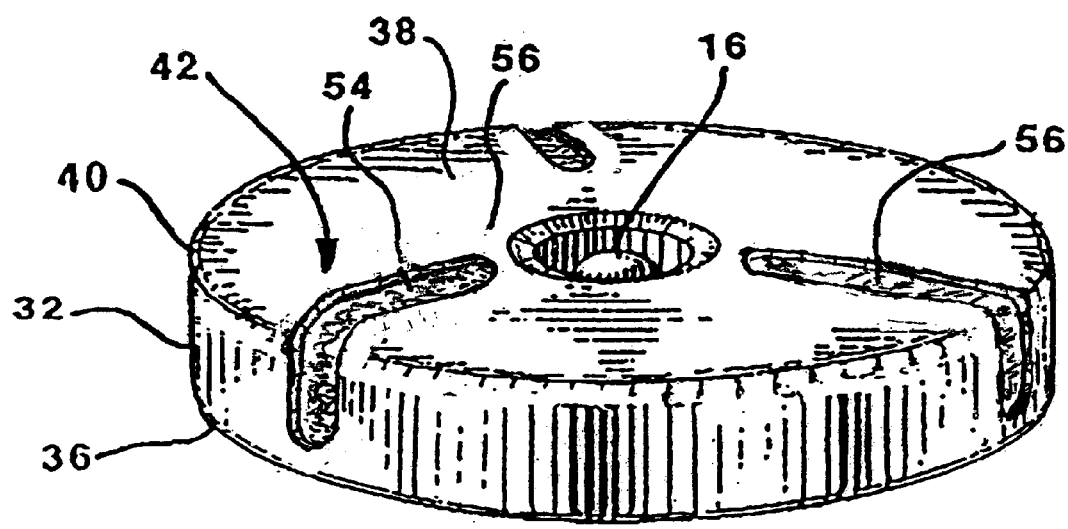
FIGS. 21 and 22 are a perspective views of other alternate embodiments of the drug pump and suture securing system of the invention.
Figure 22:
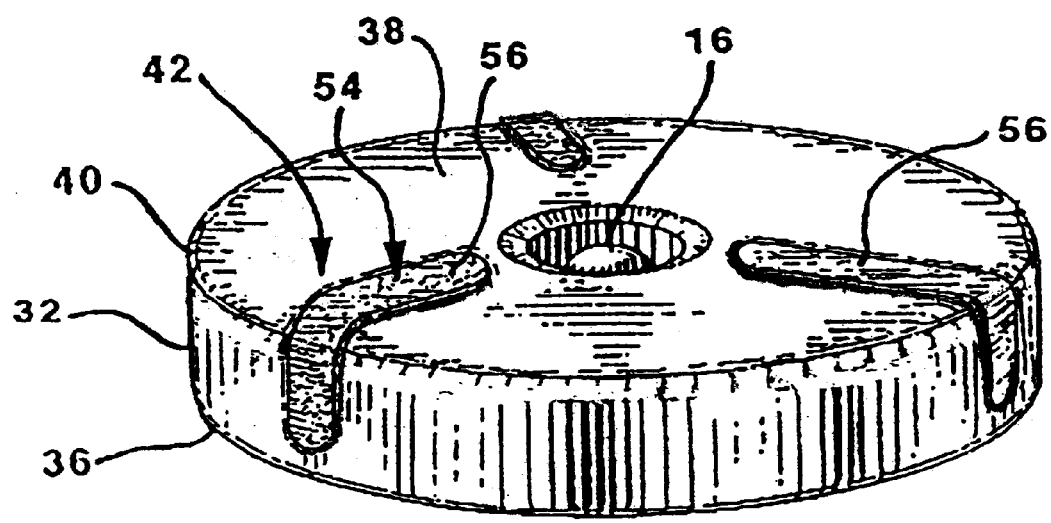

Further, the outer surface 56 of soft material 54 is preferably co-extensive with the outer dimensions of the pump 12. Although the outer surface 56 of soft material 54 is preferably co-extensive with the outer dimensions of the pump 12, the outer surface 56 need not be co-extensive with the outer dimensions of the pump 12. In other words, the outer surface 56 of soft material 54 may either be below or above the outside surface 22 of pump 12, for example, as illustrated in FIGS. 21 and 22. The key to the depth of soft material 54 and the location of outer surface 56 is that soft material 54 have a sufficient depth and be accessible to allow a suture to be placed through the material of soft material 54. Obviously, where the outer surface 56 is above the outside surface 22, the outer dimensions of pump 12 will be slightly larger than they would be if the outer surface 56 were co-extensive or below the outside surface 22 of pump 12.

In a further embodiment of the invention, both suture loops 46, in any of the forms disclosed above, may be combined with the soft material 54 described above.

The description contained herein is intended to be illustrative of the invention and not an exhaustive description. Many variations and alternatives to the disclosed embodiments will occur to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

We claim:

1. In an implantable medical device for infusing drugs, medicaments or other liquids into a body, the medical device having a reservoir for the storage of a drug, medicament or other liquid, means operatively coupled to the reservoir for dispensing the drug, medicament or other liquid, an outer shell encasing the reservoir and the means for dispensing the drug, medicament or other liquid, the outer shell having an outside surface, the medical device having an interior, the improvement comprising:

the outer surface of the outer shell being flange-less;
the outside surface having at least one depression extending toward the interior from the outside surface, the depression having a depression surface; and
at least one suture loop spanning the at least one depression and attached to the outside surface so that there is a space between the depression surface and the suture loop, the at least one suture loop being co-extensive with the outside surface surrounding the depression.

2. The medical device of claim 1 wherein the at least one suture loop is a wire.

3. The medical device of claim 2 wherein the wire is welded to the outside surface across a depression.

4. The medical device of claim 2 wherein a single wire is attached to the outside surface and crosses all depressions.

5. The medical device of claim 2 wherein at least two wires are attached to the outside surface and cross all depressions.

6. The medical device of claim 1 wherein a single suture loop spans the at least one depression and is attached to the outside surface so that there is a space between the depression surface and the suture loop.

7. The medical device of claim 1 wherein at least two suture loops span the at least one depression and are attached to the outside surface so that there is a space between the depression surface and the suture loops.

8. The medical device of claim 1 wherein the number of depressions is at least two.

9. The medical device of claim 8 wherein the at least two depressions are equally spaced around the outside surface.

10. The medical device of claim 8 wherein the at least two depressions are non-equally spaced around the outside surface.

11. The medical device of claim 1 wherein the depression surface is concave with respect to the interior of the medical device.

12. The medical device of claim 1 wherein a soft material is affixed to and in the at least one depression, the soft material capable of being bonded to or otherwise fixed in the at least one depressions and capable of holding a suture therethrough without tearing, the soft material having an outer surface.

13. In an implantable medical device for infusing drugs, medicaments or other liquids into a body, the medical device having a reservoir for the storage of a drug, medicament or other liquid, means operatively coupled to the reservoir for dispensing the drug, medicament or other liquid, an outer shell encasing the reservoir and the means for dispensing the drug, medicament or other liquid, the outer shell having an outside surface, the medical device having an interior, the improvement comprising:

the outer surface of the outer shell being flange-less;

the outside surface having at least one depression extending toward the interior from the outside surface, the depression having a depression surface; and at least one wire spanning the at least one depression and attached to the outside surface so that there is a space between the depression surface and the at least one wire, the at least one wire being co-extensive with the outside surface surrounding the depression.

14. The medical device of claim 13 wherein the number of depressions is at least two.

15. The medical device of claim 14 wherein the at least two depressions are equally spaced around the outside surface.

16. The medical device of claim 14 wherein the at least two depressions are non-equally spaced around the outside surface.

17. In an implantable medical device for infusing drugs, medicaments or other liquids into a body, the medical device having a reservoir for the storage of a drug, medicament or other liquid, means operatively coupled to the reservoir for dispensing the drug, medicament or other liquid, an outer shell encasing the reservoir and the means for dispensing the drug, medicament or other liquid, the outer shell having an outside surface, the medical device having an interior, the improvement comprising:

the outer surface of the outer shell being flange-less;

the outside surface having at least two depressions extending toward the interior from the outside surface, each depression having a depression surface, the at least two depressions being equally spaced around the outside surface; and at least one suture loop spanning at least one of the at least two depressions and attached to the outside surface so that there is a space between the depression surface and the at least one suture loop, the at least one suture loop being co-extensive with the outside surface surrounding the depression.

18. In an implantable medical device for infusing drugs, medicaments or other liquids into a body, the medical device having a reservoir for the storage of a drug, medicament or other liquid, means operatively coupled to the reservoir for dispensing the drug, medicament or other liquid, an outer shell encasing the reservoir and the means for dispensing the drug, medicament or other liquid, the outer shell having an outside surface, the medical device having an interior, the improvement comprising:

the outer surface of the outer shell being flange-less; the outside surface having at least two depressions extending toward the interior from the outside surface, each of the at least two depressions having a depression surface, the at least two depressions being non-equally spaced around the outside surface; and at least one suture loop spanning at least one of the at least two depressions and attached to the outside surface so that there is a space between the depression surface and the at least one suture loop, the at least one suture loop being co-extensive with the outside surface surrounding the depression.

19. An implantable medical device for infusing drugs, medicaments or other liquids into a body, the medical device comprising:

a reservoir for the storage of a drug, medicament or other liquid;

means operatively coupled to the reservoir for dispensing the drug, medicament or other liquid;

an outer shell encasing the reservoir and the means for dispensing the drug, medicament or other liquid, the outer shell having a flange-less outside surface, the medical device having an interior, the outside surface having at least one depression extending toward the interior from the outside surface, the at least one depression having a depression surface; and at least one suture loop spanning the at least one depression and attached to the outside surface so that there is a space between the depression surface and the at least one suture loop, the at least one suture loop being co-extensive with the outside surface surrounding the depression.

20. The medical device of claim 19 wherein the at least one suture loop is a wire.

21. The medical device of claim 20 wherein the wire is welded to the outside surface across a depression.

22. The medical device of claim 20 wherein a single wire is attached to the outside surface and crosses all depressions.

23. The medical device of claim 20 wherein at least two wires are attached to the outside surface and cross all depressions.

24. The medical device of claim 19 wherein the number of depressions is at least two.

25. The medical device of claim 24 wherein the at least two depressions are equally spaced around the outside surface.

26. The medical device of claim 24 wherein the at least two depressions are non-equally spaced around the outside surface.

27. In an implantable medical device for infusing drugs, medicaments or other liquids into a body, the medical device having a reservoir for the storage of a drug, medicament or other liquid, means operatively coupled to the reservoir for dispensing the drug, medicament or other liquid, an outer shell encasing the reservoir and the means for dispensing the drug, medicament or other liquid, the outer shell having an outside surface, the medical device having an interior, the improvement comprising:

the outer surface of the outer shell being flange-less;

the outside surface having at least one depression extending toward the interior from the outside surface, the depression having a depression surface; and wherein a soft material is affixed to and in the at least one depression, the soft material capable of being bonded to or otherwise fixed in the at least one depressions and capable of holding a suture therethrough without tearing, the soft material having an outer surface.

28. The medical device of claim 27 wherein the outer surface of the soft material is co-extensive with the outside surface of the outer shell.

29. The medical device of claim 27 wherein the outer surface of the soft material is below the outside surface of the outer shell.

30. In an implantable medical device for infusing drugs, medicaments or other liquids into a body, the medical device having a reservoir for the storage of a drug, medicament or other liquid, means operatively coupled to the reservoir for dispensing the drug, medicament or other liquid, an outer shell encasing the reservoir and the means for dispensing the drug, medicament or other liquid, the outer shell having an outside surface, the medical device having an interior, the improvement comprising:

wherein, the outside surface has at least one depression extending toward the interior from the outside surface, the depression having a depression surface; and wherein a soft material is affixed to and in the at least one depression, the soft material capable of being bonded to or otherwise fixed in the at least one depression and capable of holding a suture therethrough without tearing, the soft material having an outer surface, the soft material having an outer surface that is above the outside surface of the outer shell.

31. The medical device of claim 30 wherein the soft material is chosen from a group consisting of ETR silicone or a polymer.

32. The medical device of claim 30 wherein the polymer is chosen from a group consisting of polyurethane, polytetrafluoroethylene, polyamide or a polyester.

33. The medical device of claim 30 wherein the soft material is affixed to and in the at least one depression by adhesives.

34. The medical device of claim 30 wherein the number of depressions is at least two.

35. The medical device of claim 34 wherein the at least two depressions are equally spaced around the outside surface.

36. The medical device of claim 34 wherein the at least two depressions are non-equally spaced around the outside surface.

37. An implantable medical device for infusing drugs, medicaments or other liquids into a body, the medical device comprising:

a reservoir for the storage of a drug, medicament or other liquid;

means operatively coupled to the reservoir for dispensing the drug, medicament or other liquid;

an outer shell encasing the reservoir and the means for dispensing the drug, medicament or other liquid, the outer shell having a flange-less outside surface, the medical device having an interior, the outside surface having at least one depression extending toward the interior from the outside surface, the at least one depression having a depression surface without a through-hole through the outer shell; and wherein a soft material is affixed to and in the at least one depression, the soft material capable of being bonded to or otherwise fixed in the at least one depression and capable of holding a suture therethrough without tearing, the sort material having an outer surface.

38. The medical device of claim 37 wherein the outer surface of the soft material is co-extensive with the outside surface of the outer shell.

39. The medical device of claim 37 wherein the outer surface of the soft material is below the outside surface of the outer shell.

40. An implantable medical device for infusing drugs, medicaments or other liquids into a body, the medical device comprising:

a reservoir for the storage of a drug, medicament or other liquid;

means operatively coupled to the reservoir for dispensing the drug, medicament or other liquid;

an outer shell encasing the reservoir and the means for dispensing the drug, medicament or other liquid, the outer shell having an outside surface, the medical device having an interior, the outside surface having at least one depression extending toward the interior from the outside surface, the at least one depression having a depression surface; and wherein a soft material is affixed to and in the at least one depression, the soft material capable of being bonded to or otherwise fixed in the at least one depression and capable of holding a suture therethrough without tearing, the sort material having an outer surface, the soft material having an outer surface that is above the outside surface of the outer shell.

41. The medical device of claim 40 wherein the soft material is chosen from a group consisting of ETR silicone or a polymer.

42. The medical device of claim 40 wherein the polymer is chosen from a group consisting of polyurethane, polytetrafluoroethylene, polyamide or a polyester.

43. The medical device of claim 40 wherein the soft material is affixed to and in the at least one depression by adhesives.

44. The medical device of claim 40 wherein the number of depressions is at least two.

45. The medical device of claim 44 wherein the at least two depressions are equally spaced around the outside surface.

46. The medical device of claim 44 wherein the at least two depressions are non-equally spaced around the outside surface.

* * * * *